United States Patent [19]

Ghyczy et al.

[11] 4,332,795

[45] Jun. 1, 1982

[54] INFLAMMATION-PREVENTING PHARMACEUTICAL COMPOSITION OF ORAL ADMINISTRATION

[75] Inventors: Miklos Ghyczy; Adorjan Erdös, both of Cologne; Günter Heidemann, Geilenkirchen-Tripsrath; Götz Ritzmann, Cologne, all of Fed. Rep. of Germany

[73] Assignee: A. Nattermann & Cie. GmbH, Cologne, Fed. Rep. of Germany

[21] Appl. No.: 104,449

[22] Filed: Dec. 17, 1979

[30] Foreign Application Priority Data

Dec. 27, 1978 [DE] Fed. Rep. of Germany ....... 2856333

[51] Int. Cl.³ .................... A61K 31/40; A61K 31/685

[52] U.S. Cl. .................................. 424/199; 424/232; 424/273 P; 424/274; 424/317; 424/319; 424/356

[58] Field of Search ............................... 424/274, 199

[56] References Cited

PUBLICATIONS

Chem. Abst. 80, (1974), 128122k.

Primary Examiner—Stanley J. Friedman
Attorney, Agent, or Firm—Burns, Doane, Swecker & Mathis

[57] ABSTRACT

A novel pharmaceutical composition is provided which is suitable for the prevention of inflammation and which comprises non-steroidal inflammation-preventing compound (e.g. pyrazolones, salicylic acid derivatives, indoles, indanes, and phenylacetic acid and anthranilic acid derivatives) and at least one phospholipid.

14 Claims, No Drawings

INFLAMMATION-PREVENTING PHARMACEUTICAL COMPOSITION OF ORAL ADMINISTRATION

BACKGROUND OF THE PRESENT INVENTION

A great number of substances for the effective treatment of inflammatory illnesses, for example rheumatism, have been known for a long time. Since the inflammations are often chronic, the treatment with such inflammation-preventing active substances will usually extend over a long period of time. The non-steroidal antiphlogistic substances used for such continuous treatments very often have undesirable side effects on the digestive tract, such as, for example, in the form of gastro-intestinal bleeding and stomach ulcers as described by Y. H. Lee et al in "Arch. int. Pharmacodyn." 191, 370–377 (1971) and by K. D. Rainsford in "Agents and Actions" 1977 7(5/6), 573–77, as well as by A. R. Cooke in "Drugs" 1976, vol. 11, pages 36 to 44.

Many attempts have been made to moderate the side effects of these effective non-steroidal antiphlogistic substances by the admixture of an additional active substance. All mixtures of this type have the disadvantage that the additional substance might cause an ulcer on its own, or might even influence adversely the effectiveness of the primary non-steroidal antiphlogistic substance.

Attempts have been made, for example, to admix anticholinergic substances or pepsin inhibitors with the antiphlogistic substances (Y. H. Lee et al, "Arch. int. Pharmacodyn," 191, 370–377 (1971)). The firm of Richter Gedeon (DE-OS No. 25 24 902) proposed the admixture of salicylic acid salts with the antiphlogistic substances. However, salicylic acid salts have analgetic and antiphlogistic properties of their own and can cause strong side effects such as nausea and vomiting as well as damage of the mucous membrane of the stomach with the possibility of bleeding if administered over longer periods of time as reported by E. Mutschler in "Arzneimittelwirkungen", wissenschaftliche Verlagsgesellschaft 1970, pages 76, 77.

The Sumitomo Chemical Co. Ltd. has proposed the combination of non-steroidal antiphlogistic substances with quinazolines (see DE-OS No. 26 27 914) with the purpose of preventing the formation of peptic ulcers within the area of the digestive tract. However, these quinazolines are substances with an analgetic and antiphlogistic effect of their own. U.S. Pat. No. 3,993,767 describes mixtures of non-steroidal antiphlogistic substances with metaxalon. However, the metaxalon has a muscle-relaxing effect. See the Merck Index, Ninth edition 1976, page 772.

OBJECTS AND SUMMARY OF THE INVENTION

It is therefor the object of the present invention to develop an inflammation-preventing medicine which will substantially improve the poor compatibility of non-steroidal antiphlogistic substances without adversely influencing the inflammation-preventing effect of these active substances.

It has been found that serious side effects on the digestive tract such as damage to the mucous membrane or gastric ulcer formation by non-steroidal antiphlogistic substances can be prevented if these substances are combined in a suitable manner with phospholipids. The medicinal compositions of the present invention will therefore contain these antiphlogistic substances in conjunction with phospholipids. The phospholipids have the advantage over the previously described substances in that they are body-inherent, can be readily broken down within the body, do not promote any side effects (even if administered continuously (see J. Weihrauch, U.S. Dept. of Agriculture, quoted in National Enquirer of June 6, 1978, page 33)) and do not possess any analgetic or antiphlogistic effect of their own. The admixture of phospholipids with non-steroidal antiphlogistic substances substantially lowers the degree of side effects while the analgetic and antiphlogistic properties remain intact.

DETAILED DESCRIPTION OF THE PRESENT INVENTION

Natural as well as synthetic phospholipids can be used in the preparations of the present invention. Natural phospholipids (of plant or animal origin) such as phosphatidylcholine, phosphatidylethanolamine, phosphatidylinositol, phosphatidylserine, sphingomyeline, cephaline, lysolecithin, phosphatidylglycol, cardiolipin, and plasmalogens (which can all be obtained, for example, from the soya bean or egg) and mixtures of these phospholipids are suitable for use in the present invention. Commercially available phosphatidylcholines or phosphatidylcholine-mixtures include Phospholipon ® 100, Phospholipon ® 100 H, Phospholipon ® 80 and Phospholipon ® 45. Usable synthetic phosphatides include, for example, ditetradecanoylphosphatidylcholine, dihexadecanoylphosphatidylcholine, dioleylphosphatidylcholine or dilinolylphosphatidylcholine and especially dipalmitoylphosphatidylcholine.

The following substances are especially suitable non-steroidal antiphlogistic substances for use in the combination proposed by the invention:

Pyrazolones and especially
phenylbutazone (4-butyl-1,2-diphenylpyrazolidine-3,5-dion), and
oxyphenbutazone (4-butyl-2-(4-hydroxyphenyl)-1-p-phenylpyrazolidine-3,5-dion);
Salicylic acid derivatives such as salicylic acid
salicylic acid amide,
acetyl-salicylic acid,
benorilate (4-acetamidophenyl-o-acetylsalicylate), and
diflunisal (5-(2,4-difluorophenyl)-salicylic acid);
Indoles, especially indometacine and its analogs such as
indometacine (1-(p-chlorobenzyyl)-5-methoxy-2-methylindole acetic acid),
glucametacine (1-(p-chlorobenzoyl-5-methoxy-2-methylindole-3-yl acetic acid glucose amide),
acemetacine (1-(p-chlorobenzoyl)-5-methoxy-3-methylindole-3-acetic acid-glycolic acid-ester), and
sulindac (5-fluor-2-methyl-1-p-(methylsulphenyl)benzylidene-indene-3-acetic acid);
Phenyl acetic acid or phenyl propionic acid derivatives such as
ibuprofen (2-(4-isobutylphenyl)-propinic acid);
naproxen (2-(6-methoxy-2-naphthtyl)-propinic acid),
alclofenac (4-allyloxy-3-chlorophenyl-acetic acid),
ketoprofen (2-(3-benzylphenyl)-benzoic acid),
diclofenac (2-(2,6-dichlorophenylamino)-phenylacetic acid),
fenoprofen (2-(3-phenyloxyphenyl)-acetic acid), tolmetin (1-methyl-5-(p-toluyl)-pyrrole-2-yl-acetic acid), flurbiprofen (2-(2-fluorobiphenyl-4-ye-propionic acid), and suprofen (p-2-thenoyl-hydratropic acid) phenylproprionic acid);

Anthranilic acids and their nitrogen analogs such as flufenamino acid (N-(m-trifluoromethylphenyl)anthranilic acid), mefenamino acid (N-(2,3-dimethylphenyl)-anthranilic acid), and niflumin acid (2-(3-trifluoromethylaminolino)nicotinic acid).

The novel mixture of the present invention comprising non-steroidal antiphlogistic substances and phospholipid is particularly suitable for oral application where the molar ratio of antiphlogistic substance to phospholipid ranges from about 1:0.1 to about 1:20, and preferably from about 1:0.5 to about 1:2.

The mixture can be prepared by dissolving the antiphlogistic substance and the phospholipid in a suitable organic solvent such as methanol, ethanol or chloroform and by subsequently separating the solvent from the mixture by distillation. The antiphlogistic substance can also be dissolved in water at a suitable pH with the phospholipid being stirred into the solution. The emulsion or solution so obtained is then freed of water by lyophilic treatment, with a loose powder being obtained thereby.

The mixtures prepared in this manner can be further processed into medicines of the various standard forms of application such as, for example, in the form of pills, filled into a capsule or dispensed in the form of a granulate, a powder or a suspension. The medicine can further contain the usual quantities of carrier materials and/or diluents as well as auxiliary substances such as starch, gelatine, agar, sugar, carboxy-methylcellulose, polyvinylalcohol, magnesium stearate, sodium alginate and the like.

The advantageous effectiveness of the novel medicines proposed by the invention is demonstrated by several pharmacological tests which are listed below. The development of the ulcer was determined in accordance with B. J. R. Whittle, "Brit. J. Pharmakol." 55, 242–243 (1975), L. Mariani, "Eur. J. Toxicol. Environ." 8, 335–339 (1975), and R. Menguy & L. Desbaillets, "Proc. Soc. exp. Bio." 125, 1108.

Ten male and ten female Wistar-rats (120 to 150 grams, in weight) which have not fed for 16 hours, were used for these tests. The bleeding stomach ulcer was provoked by oral application of the active substance. After 3.5 hours, the animals are killed and the stomach extracted, opened along the wide curvature and stretched onto a "Styropor" plate. The mean ulcer factor of the test and of the control group are determined. The variation is weighted in percentages as prevention of the ulcer formation.

| Reference substances: | |
|---|---|
| chloropromazine | oral ED50 = 104.82 mg kg/KGW |
| atropinesulphate | oral ED50 = 17.06 mg kg/KGW |

The results of the tests are tabulated below in Tables I to VI:

TABLE I

Influence of Phospholipon ® 100 Upon Ulcer Development
Oral Application of Acetyl-Salicylic Acid
(Molar Ratio of Acetyl-Salicylic Acid:Phospholipon = 2:1)

| Dosage (mg/kg KGW) | n | Acetyl-Salicylic Acid Ulcer Index[a] | Acetyl-Salicylic Acid With $p^+$ Ulcer Index[a] | Variation of the Mean Ulcer Factor: Acetyl-Salicylic Acid With $p^+$ Versus Without $p^+$ (%) | Incidence of Ulcers (%) | p-Value |
|---|---|---|---|---|---|---|
| 200 | 10 | 1.20 ± 0.20 | 0.30 ± 0.09 | −83.33 | 70 resp. 20 | 0.001 |
| 400 | 10 | 1.10 ± 0.50 | 0.70 ± 0.06 | −36.36 | 50 resp. 70 | 0.10–0.01 |
| 800 | 10 | 1.20 ± 0.20 | 0.70 ± 0.06 | −41.67 | 80 resp. 70 | 0.01–0.001 |

$p^+$ = Phospholipon ® 100 (92% Phosphatidylcholin, 4% Lysophosphatidylcholin, 3% Neutrallipide, 1% water).
[a] $\bar{x} \pm s_{\bar{x}}$

TABLE II

Influence Upon Ulcer Development By Phospholipon ® 100 With
Oral Application of Phenylbutazone
(Molar Ratio of Phenylbutazone : Phospholipon = 2:1)

| Dosage (mg/kg KGW) | n | Phenylbutazone Ulcer Index[a] | Phenylbutazone With $p^+$ Ulcer Index[a] | Variation of Mean Ulcer Factor: Phenylbutazone With $p^+$ Versus Without $p^+$ (%) | Incidence of Ulcers (%) | p-Value |
|---|---|---|---|---|---|---|
| 25 | 10 | 0.70 ± 0.05 | 0.30 ± 0.04 | −57.14 | 70 resp. 30 | 0.02–0.01 |
| 50 | 10 | 1.60 ± 0.42 | 0.90 ± 0.42 | −43.75 | 60 resp. 40 | 0.01–0.001 |
| 100 | 10 | 1.80 ± 0.84 | 1.20 ± 0.84 | −33.33 | 100 resp. 90 | 0.02–0.01 |
| 200 | 10 | 1.90 ± 0.66 | 1.20 ± 0.96 | −36.84 | 80 | 0.01–0.001 |

$p^+$ = Phospholipon ® 100 (as previously defined)
[a] $\bar{x} \pm s_{\bar{x}}$

TABLE III

Influence Upon Ulcer Development By Phospholipon ® 100
With Oral Application of Indometacine
(Molar Ratio Indometacine : Phospholipon = 1:2)

| Dosage (mg/kg KGW) | n | Indometacine Ulcer Index[a] | Indometacine With p+ Ulcer Index[a] | Variation of Mean Ulcer Factor: Indometacine With p+ and Without (%) | Incidence of Ulcers (%) | p-Value |
|---|---|---|---|---|---|---|
| 5  | 10 | 1.20 ± 0.30 | 0.20 ± 0.31 | −83.33 | 70 resp. 20  | 0.02–0.01 |
| 10 | 10 | 1.90 ± 0.90 | 0.40 ± 0.07 | −78.95 | 90 resp. 40  | 0.001 |
| 20 | 10 | 1.50 ± 0.40 | 0.50 ± 0.08 | −66.67 | 100 resp. 50 | 0.001 | p+ = Phospholipon® 100 (as previously defined)
[a] $\bar{x} \pm s_{\bar{x}}$

TABLE IV

Influence Upon Ulcer Development By Phospholipon ® 45
of a Rat With Oral Application of Indometacine
(Molar Ratio of Indometacine : Phospholipon = 1:2)

| Dosage (mg/kg KGW) | n | Indometacine Ulcer Index[a] | Indometacine With Phospholipon ® 45[a] | Variation of Mean Ulcer Factor: Indometacine With p+ and Without (%) | Incidence of Ulcers (%) | p-Value |
|---|---|---|---|---|---|---|
| 5  | 10 | 2.10 ± 0.36 | 1.20 ± 0.29 | −42.85 | 80 resp. 90  | 0.1–0.05 |
| 10 | 10 | 2.20 ± 0.42 | 1.80 ± 0.25 | −18.18 | 90           | 0.5–0.4 |
| 20 | 10 | 2.30 ± 0.47 | 2.00 ± 0.36 | −13.04 | 100          | 0.5 |
| 30 | 10 | 2.70 ± 0.30 | 2.40 ± 0.30 | −11.11 | 80 resp. 100 | 0.5–0.4 | p+ = Phospholipon ® 45 (45% Phosphatidylcholine, 25% Phosphatidylethanolamine, 12% Phosphatidylinositol, 10% Sterine, 4% Lysophosphatidylcholine and Lysophosphatidylcholinethanolamine, 3% Neutrallipide, 1% water)
[a] $\bar{x} \pm s_{\bar{x}}$

TABLE V

Influence Upon Ulcer Development By Phospholipon ® 100
With Oral Application of Indometacine
(Dosage One cc per mg/kg of Body Weight (KGW))

| Proportion of Indometacine : Phospholipon ® 100 | Indometacine Ulcer Index[a] | Indometacine With p+ Ulcer Index[a] | Variation of Mean Ulcer Factor : Indometacine With p+ Versus Without p+ (%) |
|---|---|---|---|
| 1:0    | 2.60 ± 0.22 | —           | ±0 |
| 1:0.1  | —           | 1.70 ± 0.21 | −34.62 |
| 1:2.0  | —           | 0.40 ± 0.07 | −78.95 |
| 1:10.0 | —           | 1.60 ± 0.16 | −38.46 | p+ = Phospholipon ® 100 (as previously defined)
[a] $\bar{x} \pm s_{\bar{x}}$

TABLE VI

Influence Upon Ulcer Development By Phospholipon ® 100
of a Rat With Oral Application of Ibuprofen
(Molar Ratio Ibuprofen : Phospholipon = 1:1)

| Dosage (mg/kg KGW) | n | Ibuprofen Ulcer Index[a] | Ibuprofen Ulcer Index[a] With Phospholipon ® 100 | Variation of Mean Ulcer Factor : Ibuprofen With p+ and Without p+ (%) | Incidence of Ulcers (%) | p-Value |
|---|---|---|---|---|---|---|
| 5  | 10 | 0.20 ± 0.13 | 0.20 ± 0.13 | ±0     | 20          | 0.5 |
| 10 | 10 | 0.30 ± 0.15 | 0.20 ± 0.13 | −33.30 | 20 resp. 30 | 0.5 |
| 20 | 10 | 0.50 ± 0.22 | 0.40 ± 0.16 | −20.00 | 40 resp. 50 | 0.5 |
| 30 | 10 | 0.71 ± 0.30 | 0.50 ± 0.22 | −28.57 | 50 resp. 70 | 0.5 | p+ = Phospholipon ® 100 (as previously defined)
[a] $\bar{x} \pm s_{\bar{x}}$

The antiphlogistic effectiveness was determined in accordance with the rat-paw-oedema test proposed by Hillebrecht (J. Hillebrecht, "Arzneimittelforschung", 4, 607 (1954).

On one hind paw of each rat (weight 200 to 250 grams) an oedema was caused to develop by the "subplantane" application of carragenin (0.5% in a 0.9% NaCl solution) in the amount of 0.1 ml solution per paw. After the application of the test substance, its volume not to exceed 10 ml per kg of body weight, the volume of the paw is determined in an overflow ("Ueberlauf").

After three hours the final value is ascertained. The test is carried out for every dosage by using 10 test and 10 control animals of one sex and repeated with the identical number of animals of the other sex. For the purpose of evaluation, the prevention of the oedema is expressed in percentages relative to the control group.

Reference substances:

Hydrocortisoneacetate    oral ED50 =    19.00 mg/kg/KGW

-continued

| Reference substances: | |
|---|---|
| phenylbutazone | oral ED50 = 100.00 mg/kg/KGW |
| indometacine | oral ED50 = 7.24 mg/kg/KGW |

The results of these tests are listed below in Tables VII and VIII:

TABLE VII

Comparison of the Effectiveness of Indometacine and an Indometacine-Phospholipon ® 100 Mixture Applied to Rat-Paw Oedema

| Indometacine (mg/kg p.o.) | Phospholipon ® 100 mg/kg p.o. | Prevention of Oedema (%) | Number of Animals |
|---|---|---|---|
| 3.16 | — | −47.3 | 12 |
| 10 | — | −37.8 | 12 |
| 3.16 | 7.1 | −39.3 | 12 |
| 10 | 22.4 | −35.7 | 12 |
| — | 100 | −4.1 | 18 |

TABLE VIII

Comparison of the Effectiveness of Indometacine and Indometacine-Phospholipon ® 100 Mixtures Applied to Rat Paw Oedema (Dosage 0.0 mg/kg KGW, 12 Animals)

| Time:Hours Elapsed After Application of Active Substance | Indometacine | Indometacine-Phospholipon ® 100 Molar Ratios | | |
|---|---|---|---|---|
| | | 1:0.1 | 1:1 | 1:10 |
| 3 | 32 | 33 | 55 | 32 |
| 4 | 40 | 28 | 41 | 45 |
| 5 | 28 | 24 | 26 | 24 |
| 6 | 27 | 24 | 32 | 38 |

The invention is additionally illustrated in connection with the following Examples which are to be considered as illustrative of the present invention. It should be understood, however, that the invention is not limited to the specific details of the Examples.

EXAMPLE 1

4.2 grams of phenylbutazone (13.6 mMol) are suspended in 75 ml of water and admixed with 13.5 ml of caustic soda solution. Into the clear solution so obtained there are stirred 5.45 gram (7.8 mMol) of Phospholipon ® 100. The emulsion so obtained is treated lyophilically. The crystals produced are mixed with suitable additives, pressed into pills or filled into capsules.

EXAMPLE 2

1.5 grams (4.2 mMol) of indometacine are processed in a manner similar to that set forth in Example 1 to form a mixture with 4.1 of caustic soda solution, 40 ml of water and 3.35 gram (4.2 mMol) of Phospholipon ® 45 and then treated lyophilically.

EXAMPLE 3

1.88 grams (10 mMol) of acetyl-salicylic acid, 10 ml of caustic soda solution, 25 ml of water and 4 grams (5 mMol) of Phospholipon ® 100 are processed into a mixture and are then treated lyophilically.

EXAMPLE 4

Similar to Example 1, 1.88 grams (10 mMol) of acetyl-salicylic acid, 1.46 grams of DL-lysine, 30 ml of water and 1.6 grams (2 mMol) of Phospholipon ® 100 are processed into a mixture and then treated lyophilically.

EXAMPLE 5

1.43 grams (4 mMol) of indometacine and 3.2 grams (4 mMol) of Phospholipon ® 100 are dissolved in 50 ml of heated ethanol. The ethanol is then separated by distillation. The remaining substance is mixed with suitable additives pressed into pills or filled into capsules.

EXAMPLE 6

Acetyl-salicylic acid pills:
acetyl-salicylic acid: 216 mg
Phospholipon ® 100: 400 mg
aerosil: 50 mg
Na-carboxymethylcellulose: 16 mg
Cuttina H ®: 12 mg
microcrystalline cellulose: 150 mg The substances listed above are mixed, pressed and the items so pressed are coated in a manner known per se with 20 mg of hydroxypropylmethylcellulosephthalate in a coating drum.

EXAMPLE 7

Acetyl-salicylic acid capsules:
acetyl-salicylic acid: 108 mg
Phospholipon ® 80: 200 mg
talcum: 3 mg
magnesiumstearate: 3 mg
microcrystalline cellulose: 100 mg
aerosil: 25 mg The substances listed above are granulated and filled into capsules (500 mg hard-gelatin capsules).

In the case of the Examples 8–13, pills and capsules are manufactured in a manner similar to the Examples 1, 2 and 3 but employing other non-steroid, inflammation-preventing substances.

EXAMPLE 8

An indometacine pill is produced from:
30 mg of indometacine and
130 mg of Phospholipon ® 100

EXAMPLE 9

An indometacine pill is produced from:
30 mg of indometacine and
70 mg of Phospholipon ® 100H

EXAMPLE 10

Indometacine capsules are produced containing:
30 mg of indometacine
130 mg of Phospholipon ® 100

EXAMPLE 11

Phenylbutazone pills are produced containing:
105 mg of phenylbutazone
140 mg of Phospholipon ® 100

EXAMPLE 12

Ibuprofen pills are produced containing:
100 mg of ibuprofen
210 mg of Phospholipon ® 100

EXAMPLE 13

Acetyl-salicylic acid pills are produced containing:
220 mg of acetyl-salicylic acid
80 mg of dipalmitoylphosphatidylcholine All the preparations of Examples 8–13 show an improvement in compatibility and prevented side effects which normally are occurring in connection with the active substances involved.

The principles, preferred embodiments and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A method of alleviating inflammation in a mammal comprising orally administering to said mammal an effective inflammation-alleviating amount of a pharmaceutical composition comprising a phospholipid and a non-steroidal inflammation-preventing indole in a molar ratio ranging from about 0.1:1 to about 20:1, respectively.

2. The method of claim 1 wherein said indole is selected from the group consisting of indometacine, glucametacine, and acemetacine.

3. The method of claim 2 wherein said indole is indometacine.

4. The method of claim 2 wherein said indole is acemetacine.

5. The method of claim 1 wherein said phospholipid and said indole are present in molar ratios ranging from about 0.5:1 to about 2:1.

6. The method of claim 1 wherein said phospholipid is phosphatidylcholine.

7. The method of claim 1 wherein said phospholipid is phosphatidylinositol.

8. A pharmaceutical composition in a form for oral administration in the prevention of inflammation in mammals comprising an effective inflammation-alleviating amount of a phospholipid and a non-steroidal inflammation-preventing indole in a molar ratio ranging from about 0.1:1 to about 20:1, respectively.

9. The pharmaceutical composition of claim 8, wherein said indole is selected from the group consisting of indometacine, glucametacine, and acemetacine.

10. The pharmaceutical composition of claim 9 wherein said indole is indometacine.

11. The pharmaceutical composition of claim 9 wherein said indole is acemetacine.

12. The pharmaceutical composition of claim 8 wherein said phospholipid and said indole are present in molar ratios ranging from about 0.5:1 to about 2:1.

13. The pharmaceutical composition of claim 8 wherein said phospholipid is phosphatidylchloine.

14. The pharmaceutical composition of claim 8 wherein said phospholipid is phosphatidylinositol.

* * * * *